United States Patent [19]

Meyer et al.

[11] 4,325,872
[45] Apr. 20, 1982

[54] PROCESS FOR THE PREPARATION OF A 2-PYRROLIDONE

[75] Inventors: Peter J. N. Meyer, Munstergeleen; Johannes G. M. Nieuwkamp, Limbricht, both of Netherlands

[73] Assignee: Stamicarbon, B.V., Geleen, Netherlands

[21] Appl. No.: 218,465

[22] Filed: Dec. 22, 1980

[30] Foreign Application Priority Data

Dec. 21, 1979 [NL] Netherlands .......................... 7909230

[51] Int. Cl.$^3$ .......................................... C07D 207/267
[52] U.S. Cl. ............................ 260/326.5 FN; 252/412
[58] Field of Search .............. 260/326.5 FN; 252/412, 252/411 R

[56] References Cited

U.S. PATENT DOCUMENTS

| | | | |
|---|---|---|---|
| 3,095,423 | 6/1963 | Copenhaven et al. | 260/326.5 FN |
| 3,135,699 | 6/1964 | Herzog et al. | 252/412 |
| 3,198,808 | 8/1965 | Himmele et al. | 260/326.5 FN |
| 3,644,402 | 2/1972 | Takagi et al. | 260/326.5 FN |
| 3,966,763 | 6/1976 | Greene | 260/326.5 FN |
| 3,988,259 | 10/1976 | Ray | 252/412 |
| 4,036,836 | 7/1977 | Greene | 260/326.5 FN |
| 4,042,599 | 8/1977 | Greene | 260/326.5 FN |
| 4,123,438 | 10/1978 | Geurts et al. | 260/326.5 FN |
| 4,181,662 | 1/1980 | Sweeney | 260/326.5 FN |
| 4,216,151 | 8/1980 | Goettsch et al. | 260/326.5 FN |

FOREIGN PATENT DOCUMENTS 2012748 8/1979 United Kingdom .

Primary Examiner—Mary C. Lee
Attorney, Agent, or Firm—Cushman, Darby & Cushman

[57] ABSTRACT

An improved method for hydrogenating succinonitrile, optionally carrying substituents, to form 2-pyrrolidones, in the liquid phase in the presence of ammonia, using a fixed-bed catalyst wherein the catalyst may be regenerated by successively passing liquid ammonia at 75°–130° C., then hydrogen at 130°–350° C., and then liquid ammonia again at 75°–130° C. over the catalyst.

5 Claims, No Drawings

PROCESS FOR THE PREPARATION OF A 2-PYRROLIDONE

BACKGROUND OF THE INVENTION

The invention relates to a process for the preparation of a 2-pyrrolidone by catalytic hydrogenation of succinonitrile, optionally carrying substituents, conducted in the liquid phase in the presence of ammonia followed by treating the hydrogenated product obtained with water.

In U.S. Pat. No. 4,123,438 a process is disclosed which can be operated with a good yield by suspending the hydrogenation catalyst in the liquid phase. The principle drawback to this method is that after the hydrogenation the catalyst must be separated, for instance by filtration. These separation processes are costly.

According to British Pat. No. 2,012,748, this drawback can be eliminated by using a fixed-bed catalyst. In such a process the succinonitrile to be hydrogenated is dissolved in liquid ammonia, passed over the fixed-bed hydrogenation catalyst. This eliminates the need for filtration or other methods to separate the catalyst from the reaction mixture.

It has now been found, however, that application of this fixed-bed catalyst process may reduce the catalyst activity to such an extent that it is necessary to renew the catalyst. Accordingly, it is an object of the present invention to provide an improved method for the hydrogenation of the succinonitrile in a fixed-bed reactor whereby catalyst renewal is eliminated, or is required less often.

DETAILED DESCRIPTION OF THE INVENTION

According to the process of the present invention, the preparation of a 2-pyrrolidone is carried out by hydrogenation of succinonitrile, optionally carrying substituents, in the liquid phase and in the presence of ammonia using a fixed-bed hydrogeneration catalyst wherein the hydrogenation is interrupted one or more times for regeneration of the catalyst by passing liquid ammonia at a temperature in the range between about 75° C. to about 130° C., then passing hydrogen at a temperature in the range between about 130° C. to about 350° C. and then passing liquid ammonia again at a temperature in the range between about 75° C. to about 130° C. over the catalyst and then treating the hydrogenation product obtained with water.

According to the present invention, in the regeneration step an inert gas such as nitrogen or hydrogen can be passed over along with the liquid ammonia. Hydrogen is preferable since hydrogen is required both for regeneration following the passage of the liquid ammonia and for hydrogenation.

The quantity of liquid ammonia passed over the catalyst in the regeneration steps can vary and the duration of the passage of the liquid ammonia may also be varied. The quantity of liquid ammonia may for instance be varied between about 1 and about 12 kg per hour per kg catalyst. The required duration is preferably between about 0.5 and about 3 hours. A quantity of liquid ammonia greater than about 12 kg per hour per kg catalyst and/or a duration greater than about 3 hours may be employed, but this is in no way advantageous.

Following the first liquid ammonia regeneration pass over the catalyst, hydrogen is then passed over, for example a quantitiy of about 500 to about 5000 m$^3$ (calculated at 0° C. and 1 bar) per hour per m$^2$ cross-sectional area of the catalyst bed is passed over the catalyst for a period of about 2 to about 10 hours. A quantity of hydrogen greater than about 5000 m$^3$ and/or exposure to the catalyst for longer than about 10 hours may be applied, but are of no practical significance.

In the process of the present invention, after the catalyst regeneration, the hydrogenation of the succinonitrile can be continued by a known method. In the hydrogenation step, the ratio of the succinonitrile to the ammonia present in the liquid phase may be varied, for instance between about 5 and about 250 grams of the succinonitrile per about 100 grams ammonia present in the liquid phase. A substituted succinonitrile such as a succinonitrile substituted in the second or third position by an alkyl group having from 1 to 4 carbon atoms, may also be used as a starting compound.

The hydrogen partial pressure during the hydrogenation can also be varied, for instance between about 1 and about 350 bar. Preferably the hydrogen partial pressure is between about 50 and about 200 bar. The temperature is usually between about 40° C. and about 150° C. and preferably is between about 50° C. and about 130° C.

Any heavy metal hydrogenation catalyst may be employed as a catalyst for the hydrogenation of the succinonitrile. For example nickel, cobalt of palladium, optionally on a suitable carrier such as carbon, aluminium oxide or silicon dioxide. The amount of this hydrogenation catalyst used may vary between about 2 to about 90 weight percent of the carrier. The hydrogenation is usually performed with a nickel-containing catalyst.

A so-called trickle-phase reactor is suitable for conducting the hydrogenation. There under the influence of gravity, the solution of the succinonitrile in liquid ammonia flows through the fixed-bed catalyst while the hydrogen or the hydrogen-containing gas is passed countercurrently or cocurrently through the catalyst bed. Various specific catalyst loadings can be selected, for instance between about 0.1 and about 25 m$^3$ liquid per m$^3$ catalyst per hour.

After the hydrogenation of the succinonitrile, the ammonia may be wholly or partially removed from the resultant reaction mixture since the treatment of the hydrogenated product with water can be effected in either the presence or in the absence of ammonia. Various water treatment temperatures may be chosen, as in the known method, such as between about 150° and about 300° C. The quantity of water may also be varied as in the known method, such as between the stoichiometrically required quantity and about 20 moles of water per mole of succinonitrile.

The process according to the invention is illustrated further in the following non-limiting example.

EXAMPLE

In a mixer heated to 80° C., 0.2 kg succinonitrile was dissolved in 1.85 kg liquid ammonia at eleavated pressure, the solution obtained was then pumped to the top of a vertically positioned metal tubular reactor 1.5 meters long having an internal diameter of 2.54 centimeters.

A layer of 700 milliliters of catalyst was present in the reactor while 75 milliliters inert packing material (protruded metal packing, dimensions 0.6×0.16 cm) constituted a layer above the catalyst layer. The catalyst used uas a commercially available activated nickel catalyst, 50 wt.% nickel on an $Al_2O_3$ carrier, in the form of cylinders with a height of 4.2 mm and a diameter of 4.0 mm. The catalyst bulk density was 970 grams per liter.

Simultaneously with the ammoniacal solution, a compressor fed hydrogen to the top of the tubular reactor at a rate of 1400 liters (calculated at 0° C. and 1 bar) per hour while maintaining the hydrogen partial pressure in the reactor at 75 bar (total pressure 140 bar). A jacket heating means controlled the temperature in the reactor such that the reaction mixture discharged at a temperature of 85° C.

The resultant reaction mixture discharged from the bottom of the reactor was cooled to 30° C. and then separated at elevated pressure in a separator into liquid and gas. Subsequently, at atmospheric pressure in an expansion vessel, the ammonia was removed from the reaction mixture.

The reaction mixture was periodically collected for two hours for analysis. A gas chromatograph analysis of a 2-gram sample from the collected reaction mixture showed that almost no or substantially no starting compound remained. The remaining amount of the collected reaction mixture was heated along with 200 grams of water in a stirred 1-liter autoclave for 1.5 hours at 210° C. After cooling, the quantity of pyrrolidone in the hydrolyzed product was determined by gas-chromatography. The periodic analyses showed that in a 150-hour operating period the succinonitrile conversion was 95–100% with a pyrrolidone selectivity 70–75%.

After three interruptions in the hydrogenation within a 10-hour period caused by malfunctioning ammonia feed, the conversion dropped to approximately 20% over an 8-hour period. The catalyst was then regenerated as follows: liquid $NH_3$ (2 kg per hour) and hydrogen (1000 liters, calculated at 0° C. and 1 bar, per hour) were passed over the catalyst for 1.5 hours at 85° C. at a total pressure of 140 bar. Subsequently, hydrogen (1000 liters per hour, calculated at 0° C. and 1 bar) was passed over the catalyst for 4 hours at 175° C. at a total pressure of 140 bar. After the catalyst cooled to 85° C., liquid $NH_3$ (2 kg per hour) and hydrogen (1000 liters, calculated at 0° C. and 1 bar, per hour) were again passed over the catalyst for 2 hours at a total pressure of 140 bar.

When used to hydrogenate succinonitrile by the above method over a period of 200 hours this regenerated catalyst yielded results corresponding to the original succinonitrile conversion and pyrrolidone selectivity levels before catalyst regeneration.

What is claimed is:

1. In processes for the preparation of 2-pyrrolidone from succinonitrile and substituted succinonitriles carrying an alkyl group of from 1 to 4 carbon atoms by hydrogenating said succinonitrile in the presence of ammonia in the liquid phase with a fixed-bed hydrogenation catalyst and treating the hydrogenation product with water, the improvement which consists essentially in regenerating the hydrogenation catalyst by interrupting the hydrogenation and successively
   (i) passing liquid ammonia over the catalyst at a temperature of about 75° to about 130° C., then
   (ii) passing hydrogen over the catalyst at a temperature of about 130° to about 350° C. and then
   (iii) passing liquid ammonia over the catalyst again at a temperature of about 75° to about 130° C.

2. A process for the preparation of 2-pyrrolidones from succinonitrile according to claim 1 wherein said liquid ammonia pass in step (i) further includes an inert gas.

3. A process for the preparation of 2-pyrrolidones from succinonitrile according to claim 2 wherein said inert gas includes hydrogen, nitrogen and a mixture of hydrogen and nitrogen.

4. A process for the preparation of 2-pyrrolidones from succinonitrile according to claim 1 wherein said hydrogenation catalyst is selected from nickel, cobalt or palladium, optionally on a carrier.

5. A process for the regeneration of a heavy metal hydrogenation catalyst used in fixed-bed form for the hydrogenation of a succinonitrile to form a 2-pyrrolidone product which comprises interrupting said hydrogenation and successively treating said fixed-bed catalyst by
   (i) passing liquid ammonia over the catalyst at a temperature of about 75° to about 130° C., then
   (ii) passing hydrogen over the catalyst at a temperature of about 130° to about 350° C., and then
   (iii) passing liquid ammonia over the catalyst again at a temperature of about 75° to about 130° C.

* * * * *